(12) United States Patent
Alden-Danforth et al.

(10) Patent No.: US 8,663,611 B2
(45) Date of Patent: Mar. 4, 2014

(54) PERSPIRATION AND ODOR CONTROL COMPOSITIONS

(75) Inventors: Ethan Alden-Danforth, Clark, NJ (US); William Feuer, Clark, NJ (US); Nancy Williams, Clark, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 13/491,775

(22) Filed: Jun. 8, 2012

(65) Prior Publication Data

US 2013/0330290 A1 Dec. 12, 2013

(51) Int. Cl.
*A61K 8/28* (2006.01)
*A61K 8/58* (2006.01)
*A61Q 15/00* (2006.01)
*A61K 8/26* (2006.01)

(52) U.S. Cl.
USPC .............................................. 424/66; 424/68

(58) Field of Classification Search
None
See application file for complete search history.

(56) References Cited

U.S. PATENT DOCUMENTS

| 5,106,838 | A  | * | 4/1992 | Reinhart .......................... 514/59 |
| 6,503,944 | B1 | * | 1/2003 | Chanchani ..................... 514/506 |
| 2007/0116662 | A1 | * | 5/2007 | Zielinski et al. ............ 424/70.16 |
| 2009/0220444 | A1 | * | 9/2009 | Teckenbrock et al. .......... 424/66 |
| 2010/0008882 | A1 | * | 1/2010 | LaVay et al. ................ 424/70.12 |
| 2010/0247464 | A1 | * | 9/2010 | Masson et al. .................. 424/61 |
| 2012/0015064 | A1 | * | 1/2012 | Burke-Colvin et al. ....... 424/777 |

FOREIGN PATENT DOCUMENTS

FR 2854798 A1 11/2004

* cited by examiner

*Primary Examiner* — Robert A Wax
*Assistant Examiner* — Danah Al-Awadi
(74) *Attorney, Agent, or Firm* — Novak Druce Connolly Bove + Quigg LLP

(57) ABSTRACT

The present disclosure is directed to a cosmetic composition for controlling perspiration and odor. Despite being free of volatile silicones—which have garnered a bad reputation due to their ecotoxicity and bioaccumulability in aquatic species—the composition of the instant disclosure replicates the textural and sensorial benefits provided by the use of volatile silicones like cyclotetrasiloxane, cyclopentasiloxane and cyclohexasiloxane.

18 Claims, 3 Drawing Sheets

PERSPIRATION AND ODOR CONTROL COMPOSITIONS

TECHNICAL FIELD

The disclosure relates to compositions for perspiration and odor control. In particular, the disclosure relates to compositions providing perspiration and odor control that are free of highly-volatile silicones, but replicate the textural and sensorial benefits of volatile silicone-containing products.

BACKGROUND OF THE INVENTION

The present disclosure relates to compositions for perspiration and odor control that are free of highly-volatile silicones, while replicating textural and/or sensorial benefits of volatile silicone-containing products. Low molecular weight, cyclic, volatile silicones are commonly used in the cosmetics industry because of their dry, powdery feel caused by a high rate of evaporation, inter alia. Environmental groups and agencies have started to question the use of such ingredients in cosmetic compositions because these ingredients may have immediate or long-term harmful effects on the environment and/or its biological diversity. In particular, cyclic volatile silicones are thought to cause ecotoxicity and bioaccumulability in aquatic species. Typically, the end-user of a cosmetic that contains cyclic volatile silicones will allow the composition to enter the environment when removing or applying the cosmetic composition. For example, cosmetics can enter the environment when washed off the end-user during a shower or bath, or when the cosmetic is applied over a sink.

The California Office of Environmental Health Hazard Assessment (OEHHA), for example, has added cyclic siloxanes to its priority list for biomonitoring. Similarly, authorities in Canada and Europe have begun studying the environmental and health risks associated with cyclic volatile silicones. Thus, cyclic volatile silicones are unlikely to remain a viable and/or legal ingredient for cosmetic compositions because of the increased environmental scrutiny and potential hazards. However, the textural and/or sensorial properties of the cyclic volatile silicones are likely to still be desired by end-users of cosmetic compositions. It is therefore an object of the present disclosure to provide ecologically friendly and healthy alternatives that match the textural, dry after-feel of more toxic cyclic volatile silicones.

FR2854798 discloses a replacement for highly-volatile, cyclic silicones by replacing the highly-volatile cyclic silicones with their linear silicone counterparts. Even though the replacement of cyclic silicones technically represents a solution to the problem of using cyclic silicones, the corresponding linear silicones share similar hazardous chemical profile in terms of ecotoxicity and bioaccumulability to the cyclic counterparts. The approach of FR2854798 does not therefore solve the more pressing issue of finding an alternative to silicones having toxicity to the environment and aquatic life.

BRIEF SUMMARY OF THE INVENTION

The present disclosure relates to cosmetic compositions for perspiration and odor control that are free of highly-volatile silicones while replicating textural and/or sensorial benefits of such highly volatile silicone-containing products. The compositions comprise a low-volatility silicone, modified starch, and polyamide powder, with the proviso that the compositions do not contain highly-volatile cyclic or linear silicones. In another embodiment of the invention, the highly-volatile cyclic silicones include cyclotetrasiloxane, cyclopentasiloxane and cyclohexasiloxane.

In yet another embodiment, the composition further comprises one or more auxiliary ingredients selected from a group consisting of emollients; masking agents; suspension agents; crystal inhibitors; antiperspirants; deodorants; emulsifiers; film-formers; pigments, inks and lakes; stabilizers; discoloring inhibitors; dermatological agents such as sunscreen agents, anti-acne agents, anti-aging compounds; transdermal pharmaceutical compounds; perfumes; dyes; preservatives; fillers; alpha hydroxy acid; beta hydroxy acid; alpha ketoacid; antibacterial agent; sunscreen; preservative; pH adjusting agent; bleaching agent; perfume; sequestering agent; anti-dandruff agent; inhibitors; solvents; extenders; plasticizers; blowing agents; lubricants; antioxidants; adhesion promoters; fragrances; fungicides; and mixtures thereof.

In one embodiment, the composition comprises nylon-12 (Tradename Orgasol 2002 EXD NAT COS), aluminum starch octenylsuccinate (Tradename Dry Flo Plus), and dimethicone (Tradename Dow Corning SH 200 C Fluid 10 CST).

Yet another embodiment of the present invention is directed to a composition wherein the low-volatility silicone is present at a content by weight lying in the range of 2-50%; modified starch is present at a content by weight lying in the range of 0.5-25%; polyamide powder is present at a content by weight lying in the range of 0.1-10%; and one or more one auxiliary ingredient(s) are present.

Yet another embodiment of the present invention is directed to a composition wherein the low-volatility silicone is present at a content by weight lying in the range of 10-30%; modified starch is present at a content by weight lying in the range of 2-15%; polyamide powder is present at a content by weight lying in the range of 0.5-5%; and one or more one auxiliary ingredient(s) are present.

Yet another embodiment of the present invention is directed to a composition wherein the low-volatility silicone is present at a content by weight lying in the range of 15-25%; modified starch is present at a content by weight lying in the range of 5-10%; polyamide powder is present at a content by weight lying in the range of 1-3%; and one or more one auxiliary ingredient(s) are present.

A still further embodiment of the present invention is directed to a composition comprising low-volatility silicone at a content by weight of approximately 18%, modified starch at a content by weight of approximately 8%; polyamide powder at a content by weight of approximately 2%, and one or more auxiliary ingredient(s).

DETAILED DESCRIPTION OF THE INVENTION

Figure 1:
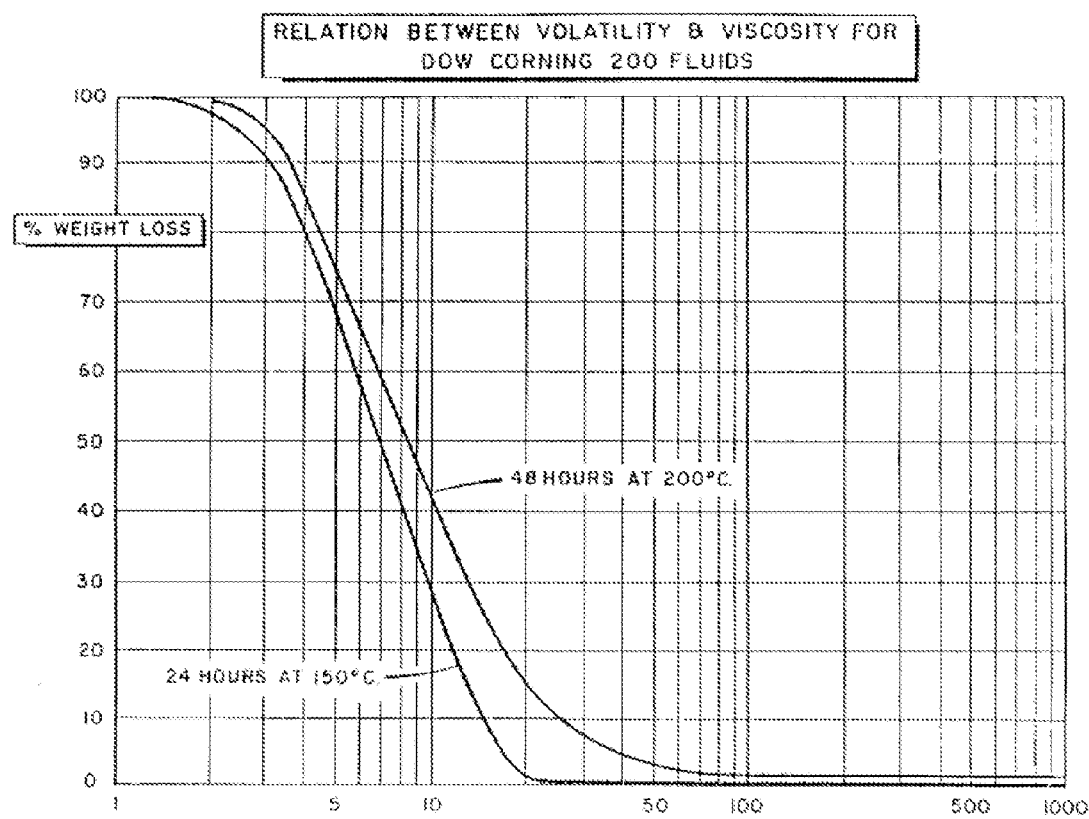
FIG. 1 is a graphical representation of typical volatility values of Dow Corning 200 Fluids.

The present invention is directed to compositions for perspiration and odor control. The compositions of the present invention do not contain highly-volatile silicones that are commonly used in the cosmetics industry, such as cyclotetrasiloxane, cyclopentasiloxane and cyclohexasiloxane. The compositions of the present invention comprise a low-volatility silicone, modified starch, and polyamide powder.

It is to be understood that both the foregoing general description and the following detailed description are exemplary and explanatory only, and are not restrictive of the invention.

The term "comprising" (and its grammatical variations) as used herein is used in the inclusive sense of "having" or "including" and not in the exclusive sense of "consisting only of." The terms "a" and "the" are used herein are understood to encompass the plural as well as the singular.

Other than in the operating examples, or where otherwise indicated, all numbers expressing quantities of ingredients and/or reaction conditions are to be understood as being modified by the term "about."

The compositions of the present invention can comprise, consist of, or consist essentially of the essential elements and limitations of the invention described herein, as well as any additional or optional ingredients, components, or limitations described herein or any otherwise useful ingredient found in compositions for perspiration and odor control.

The compositions of the present invention may be in any form as would typically be employed for compositions for perspiration and odor control, including, for example solid bars, pastes, and creams. The composition can be a molded composition or cast as a stick or disk, or the composition can be applied as a roll-on or semi-solid. Further, the composition is anhydrous (i.e., no free water added).

Surprisingly, the combination of a low-volatility silicone, modified starch, and polyamide powder replicates the textural and/or sensorial benefits of highly volatile cyclic silicone-containing products. Highly volatile cyclic silicones typically exist in the form of a liquid. The low-volatility silicone of the present invention is also typically in the form of a liquid. However, the modified starch and polyamide powder are both powders. Thus, the combination according to the present invention replicates a single volatile liquid with a mixture of a low- or non-volatile liquid and fine-grained, mattifying, oil- and water-absorbent powders. Together, the low-volatility silicone, modified starch, and polyamide powder act synergistically to provide the feel of volatile silicone-containing products. Such an approach is non-intuitive and surprising because the components do not provide the benefits of the synergistic combination when acting alone.

Low-Volatility Silicone

According to the invention, the composition comprises a low-volatility silicone. For example, the low-volatility silicone may be dimethicone, which is also referred to as polydimethylsiloxane (PDMS) and E900, inter alia. Further examples of low-volatility silicones according to the present invention may include organosiloxanes, which are known as typical compounds of organo-silicon compounds and are represented by the structural formula of $R_3SiO(R_2SiO)_nSiR_3$, $(R_2SiO)_n$, etc. As is shown by the structural formulae, organosiloxanes have a chemical structure wherein inorganic siloxane bonds of Si—O and organic groups (e.g., alkyl groups, phenyl groups, aryl groups, alkoxy groups, acyloxy groups, etc.) are bound to each other. Thus, organosiloxanes have both inorganic features of silanol bonds (Si—OH) and organic features of C—C bonds or C—O bonds.

Typical examples of low-volatility silicones favorably used in the present invention may be methylmethoxysiloxane oligomers, silicon resins of 1/3 to 2/2 in R/Si ratio having alkyl groups, fluoroalkyl groups, vinyl group, allyl group, alkenyl groups, phenyl group, xenyl group, naphthyl group, aryl groups, cyclohexyl group, cyclohexenyl group, benzyl group, aralkyl groups, aralaryl groups, epoxy groups, etc. and silicon resins having a methyl or phenyl group, tetramethyl- or ethylorthosilicate oligomers, methyl- or vinyltriacetoxysilane oligomers, and the like. These compounds may be used alone or in combination of two or more.

According to the invention, the silicone of the composition has low volatility, virtually no volatility, or no volatility. Typically, low-volatility silicones are in the liquid form at room temperature and atmospheric pressure. In one embodiment, the low-volatility silicone is Dow Corning 200 Fluid (DC-200) (i.e., polydimethylsiloxane or dimethicone). DC-200 is a commercially available, colorless silicone available in a variety of viscosities. At temperatures generally used in testing organic oils, DC-200 is virtually non-volatile at a viscosity of 100 centistokes and greater. Although low viscosity grades of DC-200 are more volatile and have considerable vapor pressure, the vapor pressure of varieties with viscosities above 50 centistokes is negligible even at temperatures of approximately 400° C. Even when DC-200 was tested at 400° F. for 48 hours, the percent weight loss of a 35 gram sample in a 150 mL beaker with a bottom area of 3 in$^2$ is less than 2% by weight. FIG. 1 shows typical volatility of DC-200 at 150° C. and 200° C.

Figure 2:
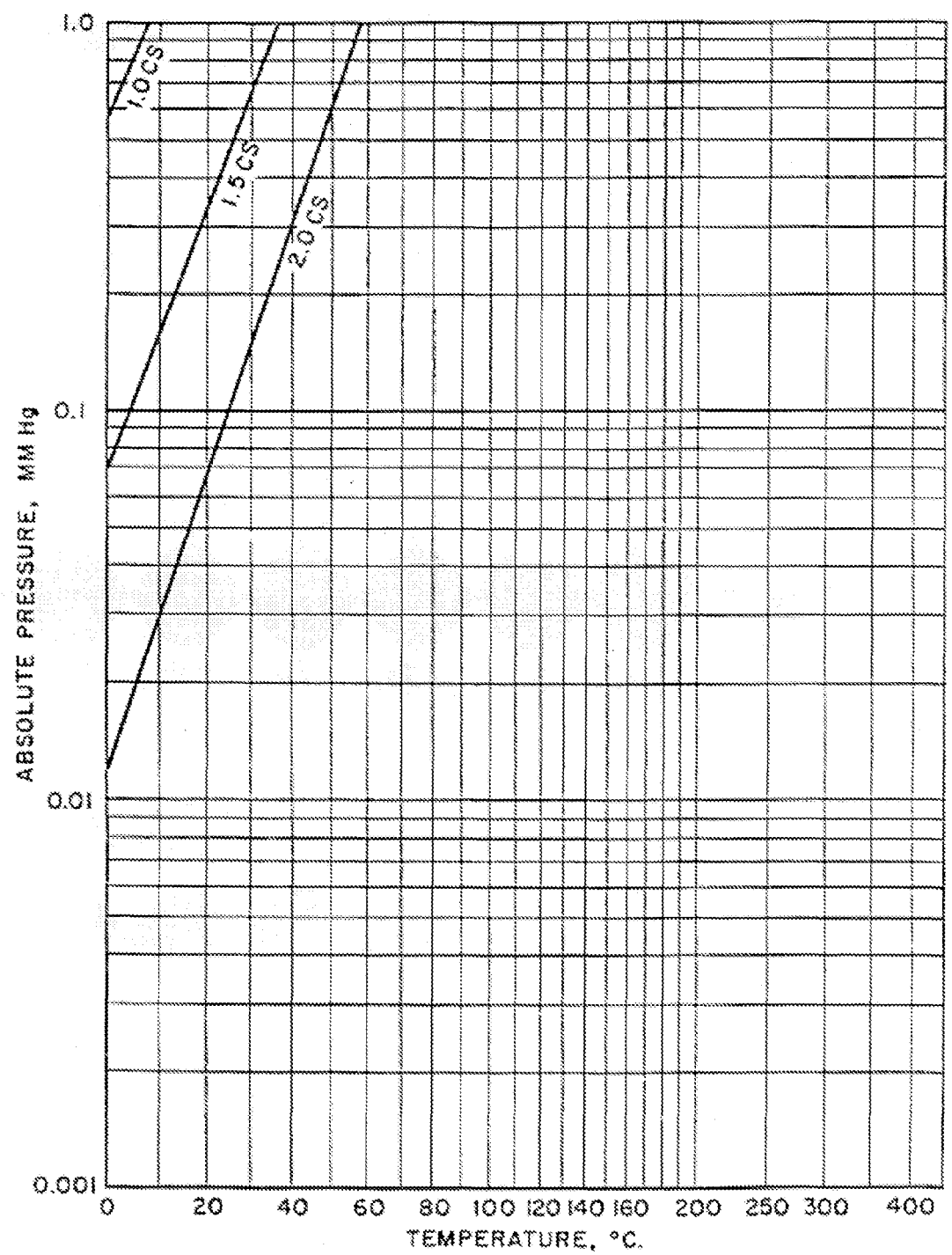
FIG. 2 is a graphical representation of vapor pressures of Down Corning 200 Fluids of varying viscosities.
Figure 3:
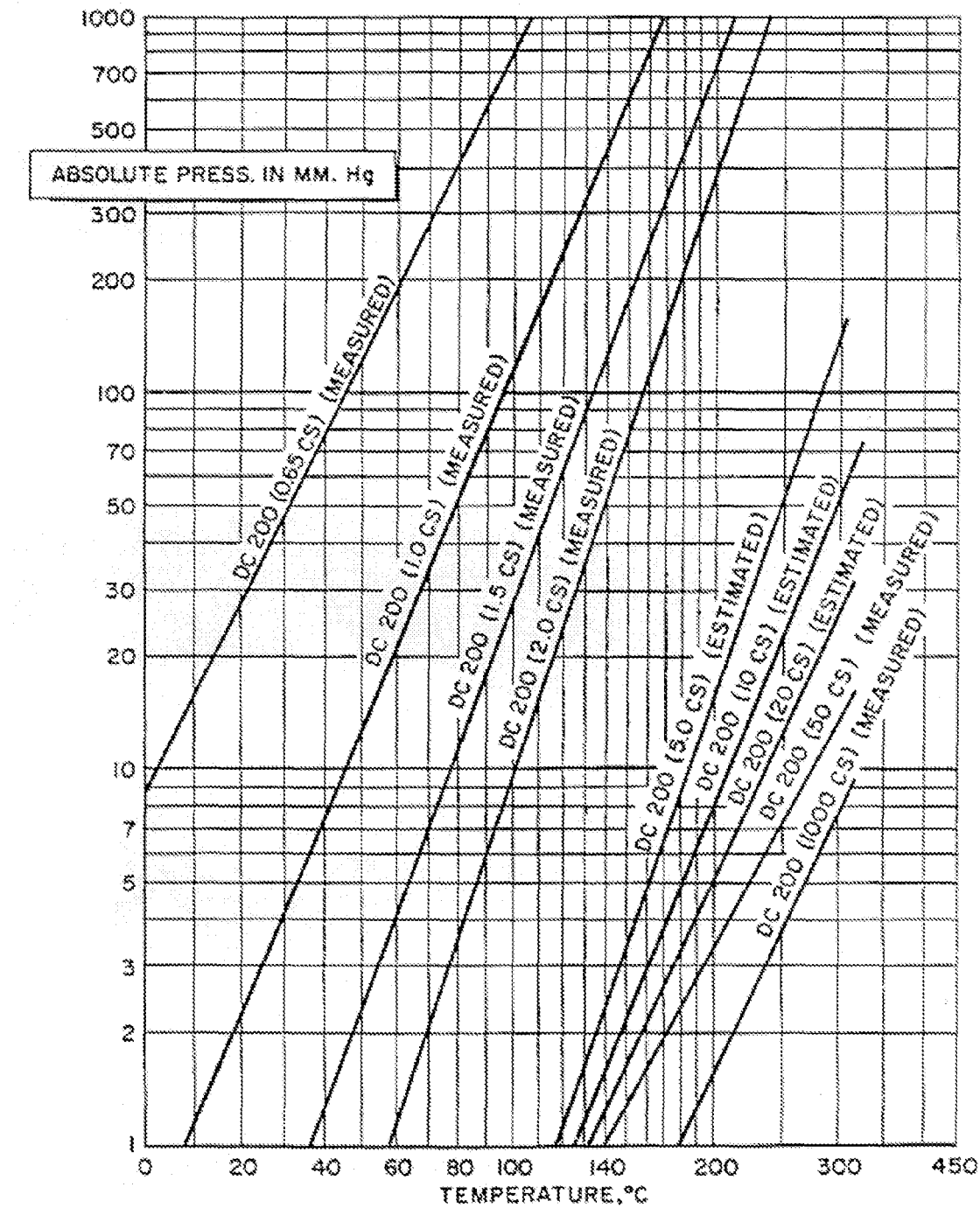
FIG. 3 is a graphical representation of vapor pressures of Down Corning 200 Fluids of varying viscosities.

Volatility is also commonly quantified by the vapor pressure of a substance. FIG. 2 depicts the vapor pressure of DC-200 fluids having viscosities of 1.0, 1.5, and 2.0 centistokes. The x axis shows the temperature in ° C. and the y axis shows the vapor pressure in mmHg (absolute pressure). FIG. 3 depicts the vapor pressure of DC-200 fluids having viscosities of 0.65, 1.0, 1.5, 2.0, 5.0, 10, 20, 50 and 1000 centistokes. The x axis shows the temperature in ° C. and the y axis shows the vapor pressure in mmHg (absolute pressure). The data in FIG. 1 and FIG. 2 can be extrapolated down to 1 mmHg and can be extrapolated below 1 mmHg by using a Cox vapor pressure chart. The vapor pressures for viscosities below 3.5 centistokes are quite accurate and typical of all production lots. The vapor pressure for higher viscosities will vary from lot to lot depending on the exact temperature and vacuum at which the fluid is stripped. If the curves for higher viscosity fluids are extrapolated to very low temperatures, the values that fall on such an extrapolated curve line may be higher values than are typical for the bulk of the fluid. These high values are due to the presence of a very small amount of low polymer silicone.

Table 1, below, shows the vapor pressure of DC-200 fluids for an assortment of viscosities. The 5 centistokes DC-200 fluid has a low vapor pressure of 6 mmHg at 156° C. but rapidly increases to 57 mmHg at 215° C. and 739 mmHg at 321° C. DC-200 fluids with increased viscosities, however, maintain low vapor pressure at increased temperatures. For example, the 50 centistoke DC-200 fluid has a vapor pressure of 150 mmHg at 375° C. and the 1000 centistoke DC-200 fluid has a vapor pressure of 53 mmHg at 350° C. Thus, it may be preferred to use DC-200 with a viscosity of 50 centistokes or greater. However, DC-200 with a viscosity of less than 50 centistokes will also provide the benefits according to the present invention. For example, in one embodiment the viscosity of the low volatility silicone can be in the range of 5 to 1000 centistokes. In another embodiment, the viscosity of the low volatility silicone can be in the range of 7 to 50 centistokes. In yet another embodiment, the viscosity of the low volatility silicone can be in the range of 8 to 12 centistokes.

TABLE 1

| Vapor Pressure For Down Corning 200 Fluids | | | | | | | |
|---|---|---|---|---|---|---|---|
| 5 cs | | 10 cs | | 50 cs | | 1000 cs | |
| °C. | mmHg | °C. | mmHg | °C. | mmHg | °C. | mmHg |
| 156 | 6 | 205 | 1 | 231 6 | 254 | 4 | |
| 190 | 25 | 233 | 22 | 277 | 11 | 304 | 8 |
| 215 | 57 | 247 | 43 | 300 | 16 | 315 | 9.8 |
| 232 | 85 | 265 | 66 | 313 | 21 | 321 | 13 |
| 321 | 739 | | | 322 | 26 | 324 | 17 |
| | | | | 330 | 31 | 332 | 20.5 |
| | | | | 336 | 40 | 337 | 27.5 |
| | | | | 340 | 47 | 342 | 35 |
| | | | | 345 | 54 | 345 | 45.5 |
| | | | | 348 | 61 | 350 | 53 |
| | | | | 353 | 71 | | |
| | | | | 356 | 80 | | |
| | | | | 358 | 91.5 | | |
| | | | | 360 | 102.5 | | |
| | | | | 363 | 113.5 | | |
| | | | | 365 | 124.5 | | |
| | | | | 372 | 136.5 | | |
| | | | | 375 | 150 | | |

Modified Starch

Modified starches according to the present invention include, for example, aluminum starch octenylsuccinate. Aluminum starch octenylsuccinate is commonly sold under the tradename DRY-FLO. Further examples of modified starches according to the present invention include: sodium starch octenylsuccinate, calcium starch octenylsuccinate, and mixtures thereof.

Further, all starches and flours are suitable for use herein and may be derived from any native source. Also suitable are starches and flours derived from a plant obtained by standard breeding techniques including crossbreeding, translocation, inversion, transformation or any other method of gene or chromosome engineering to include variations thereof. In addition, starch or flours derived from a plant grown from artificial mutations and variations of the above generic composition which may be produced by known standard methods of mutation breeding are also suitable herein. Typical sources for the starches and flours are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof.

The starch may be first nonionically derivatized using an ester or ether which is compatible with the system, particularly with the solvent. Methods of nonionically derivatization are well known in the art and may be found for example in Starch Chemistry and Technology, 2nd ed., Edited by Whistler, et al., Academic Press, Inc., Orlando (1984) or Modified Starches: Properties and Uses. Wurzburg, O. B., CRC Press, Inc., Florida, (1986).

Nonionic reagents include, but are not limited to alkylene oxides such as ethylene oxide, propylene oxide, and butylene oxide, acetic anhydride, and butyl ketene dimer. Particularly suitable nonionic reagents are the alkylene oxides, more particularly propylene oxide.

Typically, the modified starches are powders at room temperature and atmospheric pressure. The modified starch powders are fine-grained. Further, the modified starch of the present invention has a particle size distribution of 5-30 microns and an average particle size of 15 microns. Moreover, the refractive index of the modified starch is measured to be between 1.50 and 1.60 at 25° C., preferably 1.52. The modified starch powders also absorb water and oil, which helps to provide a dry feeling on the skin.

Polyamide Powder

The polyamide powder according to the present invention includes, for example, nylon-12. For example, nylon-12 of the present invention has a particle size distribution of 5-20 microns and an average particle size of 11.5 microns. The particle sizes were measured using either a Coulter Multisizer 3 via ISO 13319 or a similar method, or by scanning electron microscopy. Typically, the polyamide powders have a refractive index in the range of 1.5-1.6. However, polyamide powders with a refractive index outside of the range may function according to the present invention.

Further examples of polyamide powders according to the present invention include: nylon-6 and nylon 6,6. However, any type of polyamide resin powder would work according to the present invention.

The polyamide powder of the present invention also may act as a mattifying agent. The term "mattifying agent" is understood to mean agents that are intended to remove shine from a surface or to apply a matt to a surface.

Highly-Volatile Silicones

The highly-volatile silicones excluded from the present invention include, for example, cyclotetrasiloxane, cyclopentasiloxane, cyclohexasiloxane, and mixtures thereof. These cyclic siloxanes are commonly used in cosmetics production worldwide. Because the siloxanes are commonly used, they are entering the environment in a quantity and concentration that may have immediate or long-term harmful effects on the environmental or its biological diversity. One reason why these siloxanes are commonly used is because they impart textural and/or sensorial benefits due to, inter alia, a high rate of evaporation, which is often correlated with vapor pressure. Cyclotetrasiloxane has, for example, a vapor pressure of 1.05 mmHg at 25° C.

Similarly, cyclopentasiloxane has a vapor pressure of 0.2 mmHg at 25° C. and cyclohexasiloxane has a vapor pressure of 0.03 mmHg at 25° C. Thus, cosmetic products containing these siloxanes feel light and dry on the skin.

Further, the present compositions do not contain highly-volatile linear silicones have been taught to replace their cyclic counterparts, such as decamethyltetrasiloxane, dodecamethylpentasiloxane; 1,1,1,3,5,3-butyl, 5,5-heptamethyltrisiloxane; the 1,1,1,3,5,5,5-heptamethyl trisiloxane 3-hexyl, and mixtures thereof. Additional examples of highly volatile linear silicones include: hexamethyldisiloxane; 1,3-di-tert-butyl-1, 1,3,3-tetramethyl disiloxane; 1,3-dipropyl 1,1,3,3-tetramethyl disiloxane; heptyl pentamethyl disiloxane; 1,1,1-trimethyl 3,3,3-triethyl disiloxane; hexaethyl disiloxane; 1,1,3,3-tetramethyl 1,3-bis(2-methylpropyl)disiloxane; pentamethyl disiloxane octyl; 1,1,1-trimethyl 3,3,3-tris(1-methyl ethyl)disiloxane; 1-butyl 3-ethyl 1,1,3-trimethyl 3-propyl disiloxane; pentamethyl disiloxane pentyl; 1-butyl 1,1,3,3-tetramethyl 3-(1-methyl ethyl)disiloxane; 1,1,3,3-tetramethyl 1,3-bis(1-methyl propyl)disiloxane; 1,1,3-triethyl 1,3,3-tripropyl disiloxane; (3,3-dimethylbutyl)pentamethyl disiloxane; (3-methyl butyl)pentamethyl disiloxane; (3-methyl pentyl)pentamethyl disiloxane; 1,1,1-triethyl 3,3-dimethyl-3-propyl disiloxane; 1-(1,1-dimethylethyl) 1,1,3,3,3-pentamethyl disiloxane; 1,1,1-trimethyl 3,3,3-tripropyl disiloxane; 1,3-dimethyl 1,1,3,3-tetrakis (1-methyl ethyl)disiloxane; 1,1-dibutyl 1,3,3,3-tetramethyl disiloxane; 1,1,3,3-tetramethyl 1,3-bis(1-methyl ethyl)disiloxane; 1,1,1,3-tetramethyl 3,3-bis(1-methyl ethyl)disiloxane; 1,1,1,3-tetramethyl disiloxane 3,3-dipropyl; 1,1,3,3-tetramethyl 1,3-bis(3-methyl butyl)disiloxane; pentamethyl disiloxane butyl; pentaethyl methyl disiloxane; 1,1,3,3-tetramethyl disiloxane 1,3-dipentyl; 1,3-dimethyl-1 tetrapropyl 1,1,3,3-disiloxane; 1,1,1,3-tetraethyl 3,3-dimethyl disiloxane; 1,1,1-triethyl 3,3,3-tripropyl disiloxane; 1,3-dibutyl 1,1,3,3-tetramethyl disiloxane; pentamethyl disiloxane hexyl; octamethyltrisiloxane; 1-hexyl 1,1,3,3,5,5,5-heptamethyltrisiloxane; 1,1,1,3,3,5,5-5-octyl heptamethyl trisiloxane; 1,1,1,3,5,5,5-3-octyl heptamethyl trisiloxane; 1,1,1,3,5,5,5-heptamethyl 3-hexyl trisiloxane; 1,1,3,3,5,5-hexamethyl trisiloxane 1,5-dipropyl; 3-(1-ethylbutyl) 1,1,1,3,5,5,5-heptamethyltrisiloxane; 1,1,1,3,5,5,5-heptamethyl 3-(1-methylpentyl)trisiloxane; 1,5-diethyl 1,1,3,3,5,5-hexamethyl trisiloxane; 1,1,1,3,5,5,5-heptamethyl 3-(1-methylpropyl)trisiloxane; 3-(1,1-dimethylethyl) 1,1,1,3,5,5,5-heptamethyltrisiloxane; 1,1,1,5,5,5-hexamethyl 3,3-bis(1-methylethyl)trisiloxane; 1,1,1,3,3,5,5-hexamethyl 1,5-bis(1-methylpropyl)trisiloxane; 1,5-bis(1,1-dimethyl ethyl)-1,1,3,3,5,5-hexamethyl trisiloxane; 3-(3,3-dimethyl butyl) 1,1,1,3,5,5,5-heptamethyltrisiloxane; 1,1,1,3,5,5,5-heptamethyl 3-(3-methylbutyl)trisiloxane; 1,1,1,3,5,5,5 heptamethyl-3-(3-methylpentyl)trisiloxane; 1,1,1,3,5,5,5-heptamethyl 3-(2-methylpropyl)trisiloxane; 1,1,3,3,5,1-butyl, 5,5-heptamethyltrisiloxane; heptamethyl 1,1,1,3,5,5,5-3-propyl trisiloxane; 3-isohexyl 1,1,1,3,5,5,5-heptamethyltrisiloxane; 1,3,5-triethyl 1,1,3,5,5-pentamethyl trisiloxane; 3-butyl 1,1,1,3,5,5,5-heptamethyltrisiloxane; 3-tert-pentyl 1,1,1,3,5,5,5-heptamethyltrisiloxane; 1,1,1,5,5,5-hexamethyl trisiloxane 3,3-dipropyl; 3,3-diethyl 1,1,1,5,5 0.5-hexamethyl trisiloxane; 1,5-dibutyl 1,1,3,3,5,5-hexamethyl trisiloxane; 1,1,1,5,5,5-hexaethyl 3,3-dimethyl trisiloxane; 3,3-dibutyl 1,1,1,5,5,5-hexamethyl trisiloxane; 3-ethyl 1,1,1,3,5,5,5-heptamethyltrisiloxane; 3-heptyl 1,1,1,3,5,5,5-heptamethyltrisiloxane; 1-ethyl 1,1,3,3,5,5,5-heptamethyltrisiloxane; decamethyltetrasiloxane, 1,1,3,3,5,5,7,7-octamethyl tetrasiloxane 1,7-dipropyl; 1,1,1,3,3,5,7,7,7-nonamethyl 5-(1-methylethyl)tetrasiloxane; 1-butyl 1,1,3,3,5,5,7,7,7 nonamethyl-tetrasiloxane; 3,5-diethyl 1,1,1,3,5,7,7,7-octamethyl tetrasiloxane; 1,3,5,7-tetraethyl 1,1,3,5,7,7 hexamethyl-tetrasiloxane; 3,3,5,5-tetraethyl 1,1,1,7,7,7-hexamethyl tetrasiloxane; 1,1,1,3,3,5,5,7,7-nonamethyl 7 tetrasiloxane-phenyl; 3,3-diethyl 1,1,1,5,5,7,7,7-octamethyl tetrasiloxane; 1,1,1,3,3,5,7,7,7-nonamethyl 5-phenyl tetrasiloxane; dodecamethylpentasiloxane; 1,1,3,3,5,5,7,7,9,9-decamethyl-1,9-dipropyl pentasiloxane; 3,3,5,5,7,7 hexaethyl-1,1,9,9,9-hexamethyl-1 pentasiloxane; undecamethyl 1,1,1,3,3,5,7,7,9,9,9-5-phenyl pentasiloxane; 1-1,1,3,3,5,5,7,7,9,9,9-butyl undecamethyl pentasiloxane; 3,3-diethyl 1,1,1,5,5,7,7,9,9,9-decamethyl pentasiloxane; 1,3,5,7,9-pentaethyl 1,1,3,5,7,9,9-heptamethyl pentasiloxane; 3,5,7-triethyl 1,1,1,3,5,7,9,9,9-nonamethyl pentasiloxane; 1,1,1-triethyl-nonamethyl 3,3,5,5,7,7,9,9,9 pentasiloxane; 1-butyl 1,1,3,3,5,5,7,7,9,9,11,11,11-tridecamethyl hexasiloxane; 3,5,7,9-tetraethyl 1,1,1,3,5,7,9,11,11,11-decamethyl hexasiloxane; tetradecamethyl hexasiloxane; hexadecamethyl heptasiloxane; octadecamethyl octasiloxane; 2-[3,3,3-trimethyl 1,1-bis[(trimethylsylil)oxy]disiloxanyl]ethyl; 1,1,1,5,5,5-hexamethyl 3-(2-methylpropyl)-3-[(trimethylsilyl)oxy]trisiloxane; 3-(1,1-dimethylethyl) 1,1,1,5,5,5 hexamethyl-3-[(trimethylsilyl)oxy]trisiloxane; 3-butyl 1,1,1,5,5,5-hexamethyl 3-[(trimethylsilyl)oxy]trisiloxane; 1,1,1,5,5,5-hexamethyl 3-propyl 3-[(trimethylsilyl)oxy]trisiloxane; 3-ethyl 1,1,1,5,5,5-hexamethyl 3-[(trimethylsilyl)oxy]trisiloxane; 1,1,1-3,5,5,5-tetramethyl triethyl 3-(trimethylsiloxy)trisiloxane; 3-methyl 1,1,1,5,5,5-hexamethyl 3-[trimethylsilyl)oxy]trisiloxane; 3-[(dimethylphenylsilyl)oxy]1,1,1,3,5,5,5-heptamethyltrisiloxane; 1,1,1,5,5,5-hexamethyl 3-(2-methylpentyl) 3-[(trimethylsilyl)oxy]trisiloxane; 1,1,1,5,5,5-hexamethyl 3-(4-methylpentyl)-3-[(trimethylsilyl)oxy]trisiloxane; 3-hexyl 1,1,1,5,5,5-hexamethyl 3-[(trimethylsilyl)oxy]trisiloxane; 1,1,1,3,5,5,5-heptamethyl-3-[(trimethylsilyl)oxy]trisiloxane; 1,1,1,3,5,5,7,7,7-nonamethyl 3-(trimethylsiloxy)tetrasiloxane; 1,1,1,3,3,7,7,7-octamethyl 5-phenyl 5-[(trimethylsilyl)oxy]tetrasiloxane; 1,1,1,3,5,5,7,7,9,9,11,11,11-tridecamethyl-3-[(trimethylsilyl)oxy]hexasiloxane; 1,1,1,5,5,5-hexamethyl 3,3-bis(trimethylsiloxy)trisiloxane; 2,2,8,8-tetramethyl-5-[(pentamethyldisiloxanyl)methyl]-3, 7-dioxa-2,8disilanonane; 2,2,5,8,8-pentamethyl 5-[(trimethylsilyl)methoxy]-4,6-dioxa-2,5,8-trisilanonane; 1,3-dimethyl 1,3-bis[(trimethylsilyl)methyl]1,3-disiloxanediol; 3-ethyl 1,1,1,5,5,5-hexamethyl 3-[3-(trimethylsiloxy)propyl]trisiloxane; 1,1,1,5,5,5-hexamethyl-3-phenyl-3-[(trimethylsilyl)oxy] trisiloxane; 2,2,7,7,9,9,11,11,16,16-decamethyl 3,8,10,15-tetraoxa-2,7,9,11,16 pentasilaheptadecane; tetrakis [(trimethylsilyl)methyl]ester silicic acid; 3,5-diethyl 1,1,1,7,7,7-hexamethyl 3,5-bis[(trimethylsilyl)oxy]tetrasiloxane, 1,1,1,3,5,7,7,7-octamethyl 3,5-bis[(trimethylsilyl)oxy]tetrasiloxane; 1,1,1,3,7,7,7-heptamethyl the 3,5,5-tris [(trimethylsilyl)oxy]tetrasiloxane; 1,1,1,3,5,5,9,9,9-nonamethyl-3,7,7-tris [(trimethylsilyl)oxy]pentasiloxane; 1,1,1,3,5,7,9,9,9-nonamethyl 3,5,7-tris [(trimethylsilyl)oxy]pentasiloxane; and 1,1,1,7,7,7-hexamethyl 3,3,5,5-tetrakis [(trimethylsilyl)oxy]tetrasiloxane.

Auxiliary Ingredients

The composition may contain one or more auxiliary ingredients. Various types of auxiliary ingredients may be used in the composition of the present invention. Suitable ingredients include, for example: emollients; masking agents; suspension agents; crystal inhibitors; antiperspirants; deodorants; emulsifiers; film-formers; pigments, inks and lakes; stabilizers; discoloring inhibitors; dermatological agents such as sunscreen agents, anti-acne agents, anti-aging compounds; transdermal pharmaceutical compounds; perfumes; dyes; preservatives; fillers; alpha hydroxy acid; beta hydroxy acid; alpha ketoacid; antibacterial agent; sunscreen; preservative; pH adjusting agent; bleaching agent; perfume; sequestering agent; anti-dandruff agent; inhibitors; solvents; extenders; plasticizers; blowing agents; lubricants; antioxidants; adhesion promoters; fragrances; fungicides; and mixtures thereof.

If desired, the antipersirants are selected from the group consisting of aluminum chloride, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichloro-hydrex polyethylene glycol, aluminum sesquichloro-hydrex propylene glycol, aluminum sulfate buffered, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, and aluminum zirconium trichlorohydrex gly.

The type and amount of auxiliary ingredient to be employed will depend on the composition's ultimate use, and is to be determined by those of ordinary skill in the art.

The following examples are for illustrative purposes only and are not intended to limit the scope of the claims.

EXAMPLE 1

Antiperspirant/Deodorant Stick, Unfragranced

| INGREDIENT | WEIGHT PERCENT | WEIGHT (g) |
|---|---|---|
| Isopropyl Palmitate | 19.00 | 95.00 |
| Dimethicone | 18.00 | 90.00 |
| Stearyl Alcohol | 8.64 | 43.20 |
| Polyethylene P 400 | 6.00 | 30.00 |
| PEG-8 Distearate | 6.50 | 32.50 |
| PPG-14 Butyl Ether | 6.20 | 31.00 |
| Ozokerite | 1.75 | 8.75 |
| Polyethylene PM 500 | 1.20 | 6.00 |
| Aluminum Zirconium Tetrachlorohydrex Gly | 20.00 | 100.00 |
| Calcium Hydroxide | 0.50 | 2.50 |
| Nylon-12 | 2.00 | 10.00 |
| Aluminum Starch Octenylsuccinate | 8.00 | 40.00 |
| Perlite | 0.20 | 1.00 |
| Silk Powder | 0.01 | 0.05 |

EXAMPLE 2

Antiperspirant/Deodorant Stick, Fragranced

| INGREDIENT | WEIGHT PERCENT | WEIGHT (g) |
|---|---|---|
| Isopropyl Palmitate | 18.20 | 109.20 |
| Dimethicone | 18.00 | 108.00 |
| PPG-14 Butyl Ether | 6.20 | 37.20 |
| Disteardimonium Hectorite | 1.00 | 6.00 |
| Hydrogenated Caster Oil | 7.75 | 46.50 |
| Synthetic Wax | 2.00 | 12.00 |
| Stearyl Alcohol | 7.85 | 47.10 |
| PEG-8 Distearate | 6.50 | 39.00 |
| Aluminum Zirconium Tetrachlorohydrex Gly | 20.00 | 120.00 |
| Calcium Hydroxide | 0.50 | 3.00 |
| Nylon-12 | 2.00 | 12.00 |
| Aluminum Starch Octenylsuccinate | 8.00 | 48.00 |
| Fragrance | 2.00 | 12.00 |

Example 3

Comparative Testing

Comparative tests were performed by twelve participants, women ages 18-55, who were daily users of fragranced anti-perspirant/deodorant sticks comprising highly-volatile silicones. The tests were performed to obtain consumers' opinions, perceptions, and overall satisfaction with products containing the presently disclosed compositions. According to the testing, each participant replaced an anti-perspirant/deodorant stick comprising highly-volatile silicones with an anti-perspirant/deodorant stick comprising a composition of the present invention for four days. The participants were directed to apply the anti-perspirant/deodorant stick comprising a composition of the present invention to their underarms only.

After using the anti-perspirant/deodorant stick comprising a composition of the present invention for four days, the twelve participants were interviewed. Overall, eleven of the twelve participants felt that the anti-perspirant/deodorant stick comprising a composition of the present invention performed the way that one would expect an anti-perspirant to work. Further, additional qualities, include the textural and sensorial aspects, of the anti-perspirant/deodorant stick comprising a composition of the present invention are showing in the summary presented in the table below.

|  | Positive Aspects | Negative Aspects |
|---|---|---|
| Likes/Dislikes | Prevented wetness (9 participants) | Difficult to apply (6 participants) |
|  | Pleasant scent (6 participants) | Not creamy enough (5 participants) |
|  | Prevented odor (4 participants) | Application felt rough (3 participants) |
| Appearance | Typical look (8 participants) | — |
| Color | White (12 participants) | — |
| Texture | Smooth (6 participants) | Hard (7 participants) |
|  | Dry (3 participants) | Dry (5 participants) |
|  | Firm (3 participants) | Not creamy (4 participants) |
| Scent | Just right intensity (8 participants) | Masculine (3 participants) |
|  | Lasted all day (5 participants) |  |
|  | Floral (5 participants) |  |
|  | Clean/fresh (4 participants) |  |
| Application | Smooth (4 participants) | Not easy (8 participants) |
|  | Easy (3 participants) |  |
| Distribution | Even (8 participants) | Not even (3 participants) |
| Absorption/Dry Time | Immediate/quickly (11 participants) | — |
| Marks/Stains | No visual marks or stains (10 participants) | White stains on clothing (2 participants) |
| Skin Feel | Dry/not wet (5 participants) | Very dry (3 participants) |
|  | Light (5 participants) |  |
|  | Not sticky (3 participants) |  |
| Unpleasant Odors Throughout the Day | None (11 participants) | — |
| Wetness Throughout the Day | None (11 participants) | — |
| Lasting Effect | No wetness all day (11 participants) | — |
|  | No small all day (11 participants) |  |
| Effectiveness with Exercise/Exertion | Effective (11 participants) | — |

Further, the participants rated their overall satisfaction, the odor prevention and fragrance of the anti-perspirant/deodorant stick comprising a composition of the present invention. For the overall satisfaction and odor prevention, the participants' ratings averaged 9 out of 10 possible points. For the fragrance, the participants' ratings averaged 8 out of 10 possible points. Moreover, four of the twelve participants were more satisfied with the anti-perspirant/deodorant stick comprising a composition of the present invention as compared to their usual product, one was satisfied about the same, and seven were less satisfied.

The foregoing description illustrates and describes the disclosure. Additionally, the disclosure shows and describes only the preferred embodiment(s) but, as mentioned above, it is to be understood that it is capable to use in various other combinations, modifications, and environments and is capable of changes or modifications within the scope of the invention concepts as expressed herein, commensurate with the above teachings and/or skill or knowledge of the relevant art. The embodiments described herein above are further intended to explain best modes known by the applicants and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent applications incorporated herein by references, the present disclosure controls.

What is claimed is:

1. An antiperspirant and/or deodorant composition comprising:
    a. 15% to 25% by weight of low-volatility silicone;
    b. 5% to 10% by weight of modified starch;
    c. 1% to 3% by weight of polyamide powder; and
    d. an antiperspirant selected from the group consisting of aluminum chloride, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichloro-hydrex polyethylene glycol, aluminum sesquichloro-hydrex propylene glycol, aluminum sulfate buffered, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, and aluminum zirconium trichlorohydrex gly;
        with the proviso that the composition does not contain highly-volatile cyclic or linear silicones, and
        wherein the composition is a liquid, paste, cream, or solid bar.

2. The composition of claim 1, wherein the low-volatile silicone is dimethicone.

3. The composition of claim 1, wherein the modified starch is selected from a group consisting of aluminum starch octenylsuccinate, sodium starch octenylsuccinate, calcium starch octenylsuccinate, and mixtures thereof.

4. The composition of claim 1, wherein the polyamide powder is a mattifying agent.

5. The composition of claim 4, wherein the mattifying agent is selected from a group consisting of nylon-12, nylon-6, nylon-6,6, and mixtures thereof.

6. The composition of claim 1, wherein said composition is anhydrous.

7. The composition of claim 1, wherein the low-volatility silicone has a viscosity of approximately 5 to 1000 centistokes.

8. The composition of claim 7, wherein the low-volatility silicone has a viscosity of approximately 8 to 12 centistokes.

9. The composition of claim 1, wherein the low-volatility silicone has a vapor pressure of approximately 0.1 to 1000 mmHg (absolute pressure) at temperatures of approximately 0 to 250° C.

10. The composition of claim 9, wherein the low-volatility silicone has a vapor pressure of approximately 0.1 to 1.0 mmHg (absolute pressure) at temperatures of approximately 0 to 60° C.

11. The composition of claim 1, wherein the low-volatility silicone has a vapor pressure that is negligible at temperatures of approximately 400° C. and greater.

12. The composition of claim 1, wherein the low-volatility silicone is dimethicone, the modified starch is aluminum starch octenylsuccinate; and the polyamide powder is nylon-12.

13. The composition of claim 1, wherein the composition comprises:
    a. approximately 18% by weight of low-volatility silicone;
    b. approximately 8% by weight of modified starch;
    c. approximately 2% by weight of polyamide powder; and
    d. an antiperspirant selected from the group consisting of aluminum chloride, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichloro-hydrex polyethylene glycol, aluminum sesquichloro-hydrex propylene glycol, aluminum sulfate buffered, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, and aluminum zirconium trichlorohydrex gly.

14. The composition of claim 13, wherein the low-volatile silicone is dimethicone, the modified starch is aluminum starch octenylsuccinate, and the polyamide powder is nylon-12.

15. The composition of claim 1, wherein the form of the composition is selected from the group consisting of a molded composition, a cast composition, a roll-on composition, and a semi-solid composition.

16. An antiperspirant and/or deodorant composition comprising:
    a. approximately 18% by weight of dimethicone;
    b. approximately 8% by weight of aluminum starch octenylsuccinate;
    c. approximately 2% by weight of nylon-12; and
    d. an antiperspirant selected from the group consisting of aluminum chloride, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichloro-hydrex polyethylene glycol, aluminum sesquichloro-hydrex propylene glycol, aluminum sulfate buffered, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, and aluminum zirconium trichlorohydrex gly;
        with the proviso that the composition does not contain highly-volatile cyclic or linear silicones having a vapor pressure of 0.03 mmHg to 1.05 mmHg at 25° C., and
        wherein the composition is a liquid, paste, cream, or solid bar.

17. A method for treating body odor comprising applying a composition according to claim 1 to the body.

18. A method of claim 17, wherein the composition is applied to the underarm.

* * * * *